United States Patent
Romare

(10) Patent No.: US 6,293,931 B1
(45) Date of Patent: Sep. 25, 2001

(54) ABSORBENT PRODUCT

(75) Inventor: Anette Romare, Mölndal (SE)

(73) Assignee: SCA Hygiene Products AB, Goteborg (SE)

( * ) Notice: Subject to any disclaimer, the term of this patent is extended or adjusted under 35 U.S.C. 154(b) by 0 days.

(21) Appl. No.: 09/343,704

(22) Filed: Jun. 30, 1999

(30) Foreign Application Priority Data

Sep. 2, 1998 (GB) .................................................. 9819140

(51) Int. Cl.⁷ ....................................................... A61F 13/15
(52) U.S. Cl. .................... 604/385.01; 604/379; 604/380; 604/385.101
(58) Field of Search .................................. 604/379, 380, 604/385.01, 385.101, 385.21, 385.22, 385.23

(56) References Cited

U.S. PATENT DOCUMENTS 4,623,341    11/1986   Roeder .
5,591,148 *  1/1997    McFall et al. ........................ 604/378
5,716,351 *  2/1998    Roe ................................... 604/385.1

FOREIGN PATENT DOCUMENTS 0 483 730 A1   5/1992   (EP) .
2 272 157 A    5/1994   (GB) .
WO 95/27457   10/1995   (WO) .

* cited by examiner

Primary Examiner—Aaron J. Lewis
Assistant Examiner—Jamisue A Webb
(74) Attorney, Agent, or Firm—Burns, Doane, Swecker & Mathis, L.L.P.

(57) ABSTRACT

An absorbent article 10 which has a dimension in a longitudinal direction which is greater than its dimension in a transverse dimension. The absorbent article 10 comprises a liquid pervious top sheet 1 a liquid impervious back sheet 2 vertically below the top sheet, and an absorbent core 3 provided between the top sheet and the back sheet. The absorbent core has a first unconstrained form in which a section 6 of the absorbent core forms a protrusion from the remainder of the absorbent core in the vertical direction towards the top sheet, and a second unconstrained form in which the absorbent core has no substantive protrusion in the vertical direction. The absorbent core is capable of being changed between the first and second forms.

15 Claims, 1 Drawing Sheet

ABSORBENT PRODUCT

FIELD OF THE INVENTION

The invention relates to absorbent articles. Absorbent articles are generally worn in the crotch region and may be in the form of an absorbent garment or an insert for use in a garment. Examples of absorbent articles include sanitary napkins, diapers, incontinence pads etc. Such articles include an absorbent core capable of absorbing a large volume of human exudates. The invention in particular relates to sanitary napkins.

BACKGROUND OF THE INVENTION

Sanitary napkins generally include a top sheet which is worn next to the wearer. The top sheet is permeable to allow bodily liquids to pass through it. The liquids which pass through the top sheet are absorbed in an absorbent core which lies underneath the top sheet. In order to protect the clothes of the wearer, an impervious backing sheet is provided which prevents the passage of bodily fluids.

Many sanitary napkins have a generally planar shape. However, in order to better fit to the shape of the body of the wearer it has been proposed to provide a three-dimensional shape which includes a form of a hump so that a central portion is raised out of the plane of the napkin relative to the surrounding portion towards the wearer. The hump is intended to allow the sanitary napkin to conform more closely to the shape of the wearer and to provide enhanced absorption capacity in the wetting area. In particular, the sanitary napkin should continue to conform to the shape of the wearer even when the wearer adopts different positions or performs different activities. One example of such a hump-shaped sanitary napkin is taught in WO-A-95 27457. In accordance with the teachings of this document a sanitary napkin is provided with a lifting member for biassing a central core segment towards a position in which the central segment is raised relative to side segments.

Not all wearers however find the presence of a raised central segment to be comfortable. For certain types of activities, e.g. cycling, such a three dimensional shape may not be found comfortable. Also the external appearance of such a raised central segment may cause embarrassment to the user and hence not be acceptable to all wearers.

SUMMARY OF THE INVENTION

In accordance with the invention there is provided an absorbent article in accordance with claim 1.

A device in accordance with the invention allows the user to choose the form in which the article is to be used. The first form has a raised portion such as to form a hump type of shape, whilst the second portion presents a generally flat form towards the user. Thus in one situation the absorbent article may be used in the first form in which a better fit to the wearer may be achieved. In another situation the absorbent article may be used in the second form which produces greater comfort in that situation.

An unconstrained form is a form which the absorbent article will keep when the force is removed which has changed the article to that form.

As referred to herein a longitudinal direction is intended to mean a direction along the largest dimension of the article. A vertical direction is intended to be a direction perpendicular to the longitudinal direction and in a direction from the backing sheet to the top sheet so that in the case of a sanitary napkin the vertical direction is towards the urogenital area of the body of the user when in use. A transverse direction is a direction perpendicular to both the longitudinal and vertical directions. A transverse cross-section is intended to mean a cross-section in a plane which is generally perpendicular to the longitudinal direction.

Although described with respect to a sanitary napkin, the invention may be applied to all forms of absorbent articles for which it is desired to provide a form fitting to the body of the wearer, in particular female wearers, e.g diapers, incontinence garments etc.

Figure 6:
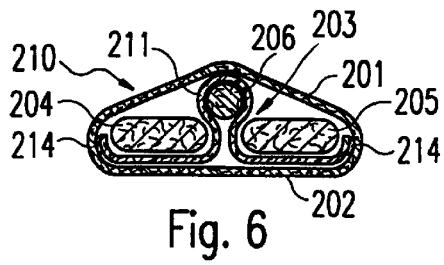

FIG. 6 shows a transverse cross-section of a third embodiment of a sanitary napkin according to the invention In a first embodiment, as shown in FIGS. 1, 2, 3A and 3B, there is shown an absorbent article, in this case in the form of a sanitary napkin 10. The napkin has a generally elongate shape, such as an hourglass shape or, as shown here, an elongated oval shape with two generally straight side edges and curved end portions. The napkin includes a top sheet 1 which is intended to be worn facing the wearer. The top sheet 1 is formed from a material which is permeable to bodily fluids, i.e. urine, blood etc. A back sheet 2 is provided which may be attached to the top sheet along their peripheral edges. The back sheet 2 may comprise a flexible material which may be tear-resistant, non-woven, perforated plastics film, netting etc. or a combination of two or more of these. The material of the back sheet may have elastic properties to allow it to stretch. The back sheet 2 is intended to be worn facing away from the wearer and serves to protect the clothes of the wearer from bodily fluids which are taken into or absorbed by the absorbent article. The back sheet 2 is made from fluid impervious or fluid resistant material, such as polyethylene film, to prevent the passage of bodily fluids therethrough. The back sheet 2 typically may include thereon fastening means, such as adhesive or mechanical fasteners, to assist it in maintaining the position of the absorbent article with respect to the user's undergarment. Optionally, the absorbent article may include side flaps of material which may be included for folding around the user's undergarment to help maintain the position of the absorbent article.

Between the top sheet 1 and the back sheet 2 an absorbent core, generally indicated by reference numeral 3, is positioned. The absorbent core 3 serves to absorb bodily fluids which have passed through the permeable top sheet 1. Any suitable material or combination of materials, such as are known in the art, may be used for the core. The material may advantageously have good absorbent properties, for example by the inclusion of superabsorbent materials. Alternatively or in addition the material may also have good wicking properties, such as material including cellulosic fibres, to facilitate transport of the fluid to absorbent material in the absorbent core 3.

Figure 3A:
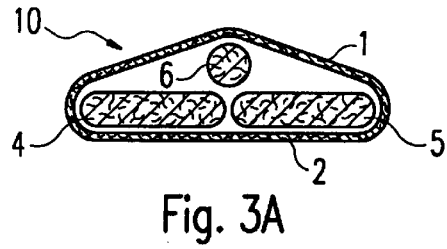
FIG. 3A shows a transverse cross-section of the first embodiment of a sanitary napkin through the line III—III of FIG. 1.
Figure 3B:
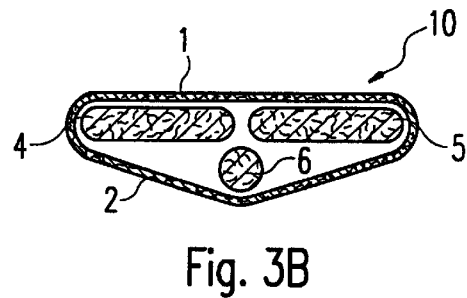
FIG. 3B shows the embodiment of FIG. 1 in a cross-section view similar to FIG. 3A, where the article is however in the second form which it may assume.

The absorbent core 3, in this instance, has three sections 4, 5, and 6. Two elongate side sections 4, 5 are shown which extend longitudinally along the longitudinal sides of the absorbent article 10. The side sections 4, 5 may extend the whole length of the absorbent article or alternatively may extend only a part of the length. When the side sections 4, 5 do not extend the whole length of the garment further absorbent end sections 8, 9 of the absorbent core are provided at the front and rear ends respectively. An intermediate, section 6 of the absorbent core 3 is provided, as indicated in dashed lines in FIG. 1. This intermediate section 6 is able to be moved in the vertical direction relative to the side sections 4, 5 In one position as shown in FIG. 3A the intermediate section 6 occupies a position which is higher than the side sections 4, 5. In this first position of the intermediate section 6, the absorbent article 10 takes on a first unconstrained form. In a second position, as shown in FIG. 3B, the intermediate section 6 occupies a position which is lower than the side sections 4, 5. In this second position of the intermediate section 6, the absorbent article takes on a second unconstrained form. Thus, the intermediate section 6 is movable from a position substantially on one side of the remainder of the absorbent core 3 to a position substantially on the other side of the remainder of the absorbent core, so as the change the absorbent core from the said first form to the said second form. The internal faces of the side sections 4, 5 which face each other form a gap therebetween. The minimum width of the gap can vary between zero, when the faces touch each other, up to a value which is equal to or less than the maximum width of the intermediate section 6 in the transverse direction. The movement takes place through the gap or disconnected portion 12 (see FIG. 5) of the absorbent core between the side sections 4, 5. A gap is formed by space between the two side sections 4, 5. By disconnected portion is meant a portion of the core where the fibres touch each other but do not interconnect so that they may under force be moved apart to form a gap, the gap substantially disappearing after removal of the force.

The intermediate section 6 may be unconnected with the remainder of the core, as shown in the figures, or may be attached to one or both side sections 4, 5; alternatively or additionally the intermediate section 6 may be attached to one or both end sections 8, 9. The attachment of the intermediate section 6 may advantageously be achieved by a piece or pieces of material which have sufficient length or elasticity to allow the movement required of the intermediate section 6. By attaching the intermediate section to a part of the remainder of the core it is ensured that it cannot move too far from its desired central position. The intermediate section 6 may be attached to the remainder of the core by a material having good wicking properties such as a material including cellulosic fibres.

The wicking material serves to distribute fluids absorbed in the intermediate section to the remainder of the absorbent core, i.e. the side sections 4,5 and/or end sections 8, 9.

As shown in FIG. 3A the intermediate section 6 has a circular transverse cross-section. However, other cross-sections having the same dimensions in two perpendicular directions are possible, e.g. square. It is also possible for the transverse cross-section dimensions in two perpendicular directions to be different, e.g. rectangular, triangular or oval.

The intermediate section 6 is movable between the said two positions so as to allow the absorbent core to take on at least two different forms. In a first form, as shown in FIG. 3A, the sanitary napkin 10 presents a protrusion extending vertically towards the wearer. In a second form, as shown in FIG. 3B, the sanitary napkin presents a protrusion extending away from the wearer without any substantial protrusion extending towards the wearer. The movement of the intermediate section 6 between the first and second positions can be effected manually by the wearer. In order to carry out this movement the wearer may push the intermediate section 6 between the side sections 4, 5. The side sections are able to move apart due to elastic properties of the top sheet 1 and/or the back sheet 3 and/or the compressive properties of the side sections 4, 5 and/or end sections 8, 9 to form a gap. Also the intermediate section may have compressive properties, preferably resiliently compressible fibrous wadding or foam, so that it may be squeezed smaller to facilitate the movement. The intermediate section 6 is moved through the said gap to the other side of the absorbent core. The intermediate section 6 may optionally be moved only into the gap formed between the side and end sections and remain therein. Thus, the sanitary napkin then has a planar shape. In this position a third form of the sanitary napkin results, in which there is also no substantial protrusion extending towards the wearer.

Although shown in a position in the centre of the absorbent article as seen in the transverse direction, the intermediate section 6 may alternatively be provided in a position nearer to one or other of the longitudinal sides.

Figure 1:
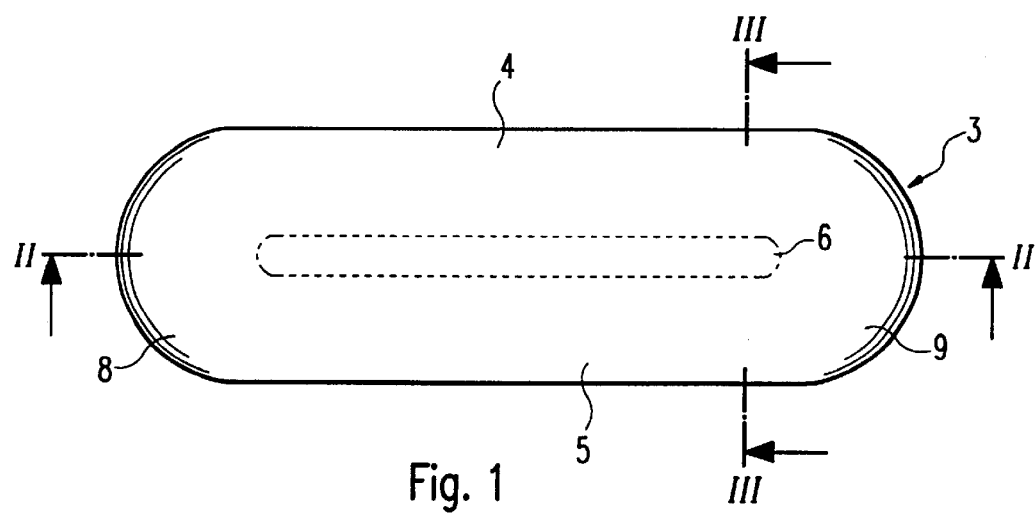
FIG. 1 shows a plan view from above of the absorbent core of a first embodiment of the invention.
Figure 2:
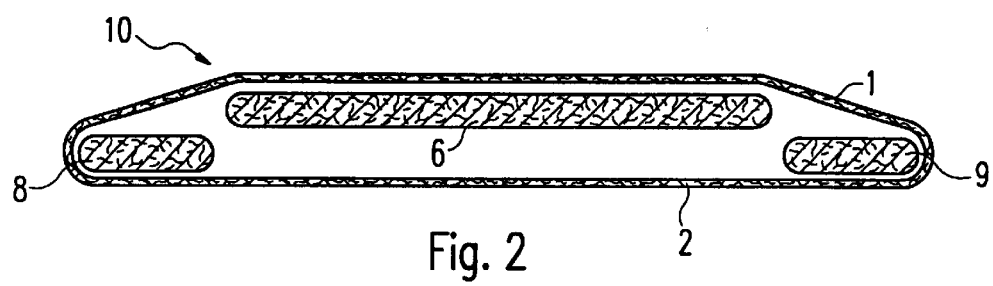
FIG. 2 shows a longitudinal cross-section of the first embodiment of the invention through a line II—II of FIG. 1.

The intermediate section 6 may extend almost the whole length of the absorbent article or, as shown in FIG. 2, only part of the length. Although it is shown in FIG. 2 in the longitudinal centre, the intermediate section 6 may alternatively be provided nearer to the front end of the sanitary napkin or nearer to the rear end. This asymmetric positioning of the intermediate section may serve to provide a better fit to the user by providing the protrusion as close as possible to the most suitable position. In addition, the extra absorbent capacities of the intermediate section may thus be provided nearer to where they are required. The end sections 8, 9 may optionally be formed integrally with the side sections 4, 5 to form a single continuous section surrounding the intermediate section 6, as shown in FIG. 1

In the second position of the intermediate section 6, there is formed by the top sheet 1 a channel 7. This channel serves to distribute bodily fluids over the length of the sanitary napkin. The presence of the channel improves the utilisation of the absorbent material in the absorbent core. Exudates may initially flow within the channel before passing through the pervious top sheet. The exudate will then pass through the top sheet at a point remote from where the exudate is produced, thus coming into contact with less saturated absorbent material. The surface of the top sheet facing the intermediate section 6 may be attached to the intermediate section to aid the formation of the channel. When the intermediate section is moved to the second position as shown in FIG. 3B, the top sheet is pulled between the side sections 4, 5 of the absorbent core and thus forms the channel 7.

Figure 4A:
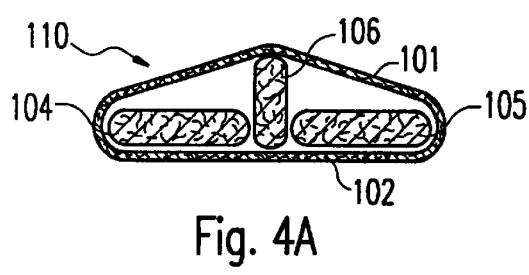
FIGS. 4A and 4B show transverse cross-sections of a second embodiment of a sanitary napkin according to the invention in two different forms which it may assume in use.
Figure 4B:
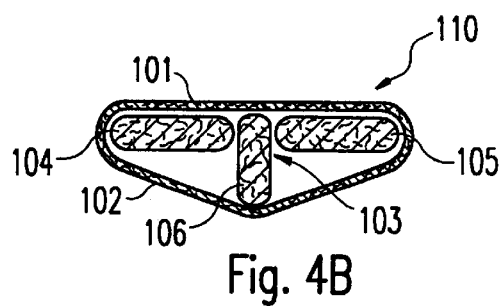

In a second embodiment of the sanitary napkin 110 of the invention, as shown in FIGS. 4A and 4B, the intermediate section 106 has a transverse cross-section in which the dimensions in two perpendicular directions are different. Thus the intermediate section 106 has a dimension in the vertical direction which exceeds the dimension of the remainder of the absorbent core 103 in the same direction. In this case, part of the intermediate section 106 of the absorbent core remains between the two side sections 104, 105 of the absorbent core 103. This ensures that the width of the sanitary napkin does not change as the intermediate section moves from the first position as shown in FIG. 4A to the second position as shown in FIG. 4B. It also means that the movement of the intermediate section may be easier, as it is not necessary for the user to find the position where the side sections meet. It is also possible in this embodiment for the intermediate section to assume intermediate positions between the first and second positions. This allows variation in the extent by which the form of the sanitary napkin is changed. Although shown as having a cross-section including straight sides and curved ends the intermediate section 106 may assume any shape having one dimension greater than another perpendicular dimension, for example rectangular, elliptical etc.

As shown in FIGS. 4A and 4B, the second embodiment, like the first embodiment, includes a permeable top sheet 101 and a fluid impervious or fluid resistant back sheet 102.

The absorbent core of the second embodiment may have any of the shapes of the side and end sections 4, 5, 8, 9 of the absorbent core as set out with respect to the first embodiment. In addition, the length and positioning of the intermediate section 106 may be as set out with respect to the first embodiment.

Figure 5:
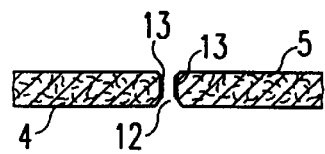
FIG. 5 shows a transverse cross-section of a part of a sanitary napkin according to the invention showing the positioning of high-friction or low-friction surfaces.

The intermediate section 6, 106 moves from the first position to the second position through the gap or disconnected portion 12 formed between the two side sections 4, 5, 104, 105. The intermediate section 6, 106 thus has a transverse dimension which is less than the width of any gap formed between the two side sections. In order to allow the intermediate section 6, 106 to move smoothly through the gap or disconnected portion, low-friction surfaces 13, as illustrated in FIG. 5, may be provided. The low-friction surfaces may be positioned on the inner side edges of the side sections 4, 5, 104, 105, which have sliding-touching contact with the intermediate section when the intermediate section is moved between the first and second positions or vice-versa. The low-friction surfaces may be provided at one or several regions along the longitudinal length of the sides. Alternatively, one or more low-friction surfaces may be provided at least on the part of the intermediate section which have sliding-touching contact with the side sections of the absorbent core when the intermediate section is moved between the first and second positions. By low-friction surfaces is meant surfaces of any material which enhance the sliding properties of the intermediate and side sections relative to each other. The surfaces may be provided by means of a coating of a suitable substance or attaching a portion of material having the required surface properties. A non-limiting example of a low-friction surface material is polytetrafluoroethylene (PTFE).

In embodiments of the invention, such as the second embodiment, where it is desirable to hold the intermediate section in a position in contact with the inner sides of the side section then the surfaces 13 could be formed of high friction material, to reduce the tendency to move when subject to external pressure.

FIG. 6 shows a third embodiment of the invention. The embodiment is shown as a modification of the first embodiment. Its principles can however equally be applied to the other embodiments of the invention. In this embodiment the absorbent article 210 is provided with a top sheet 201, a back sheet 202, an absorbent core 203, side sections 204, 205, end sections and intermediate section 206 as already described with respect to the first embodiment. In addition a sheet of material 211 is provided. The sheet is positioned on the side of the intermediate section 206 which is nearer to the wearer in use and on the side of the side sections 204, 205 which is away from the user in use. The sheet 211 may be attached to one of the top sheet or the back sheet. In the illustrated example the sheet 211 is attached to the back sheet 202 as indicate at 214. The sheet 211 may be attached by adhesive, friction or any other suitable means. The sheet 211 may alternatively be attached to the side sections 204, 205, also by means of adhesive, friction, or other suitable means. The sheet 211 is of suitable dimensions and suitably attached to allow the intermediate section 206 to move from the side of the absorbent core further from the wearer in use to the side of the absorbent core 203 nearer to the wearer in use in passing through the gap provided in the absorbent core. The dimensions of the sheet 211 may be chosen to ensure that the intermediate section is unable to move substantially in a lateral direction towards one or other of the side sections 204, 205, when in the position nearer to the wearer. The sheet 211 need not extend the whole length of the intermediate section 206. The sheet could extend less than half the length of the intermediate section, and there could be more than one sheet provided, with two or more sheets at spaced intervals along the length of the intermediate section 206. The sheet 211 is preferably formed of permeable material to allow the intermediate section 206 to function as an absorbent body. Non-woven materials, perforated plastics films, netting etc. are suitable materials for the sheet 211

When the intermediate section 6, 106, 206 is moved from a first position to a second position, it may be necessary for a gap to be created between the side sections 4, 5, 104, 105, 204, 205. The top and back sheets 2, 3, 102, 103, 202, 203 are made of materials of sufficient elasticity to allow such a gap to be created. Alternatively, or in addition, the material of the side sections may have sufficient compressibility to allow the gap to be created by reducing their transverse dimensions to create the necessary gap. Furthermore, the intermediate section 6, 106, 206 may be formed of resiliently compressible material to facilitate its passing between the side sections.

What is claimed is:

1. An absorbent article having a dimension in a longitudinal direction which is greater than its dimension in a transverse direction, the absorbent article comprising:
   a liquid pervious top sheet;
   a liquid impervious back sheet provided below the top sheet; and
   an absorbent core provided between the top sheet and the back sheet, the absorbent core having a first unconstrained form in which a section of the absorbent core forms a protrusion from the remainder of the absorbent core in the direction toward the top sheet, and a second unconstrained form in which the absorbent core has no substantive protrusion in the direction toward the top sheet, the absorbent core being capable of being changed between the first and second forms.

2. An absorbent article according to claim 1, wherein the protrusion is elongate in the longitudinal direction.

3. An absorbent article according to claim 1, wherein the absorbent core includes an intermediate section which is movable relative to the remainder of the absorbent core and which forms said protrusion, the absorbent core being changeable between said first and second forms by manual movement of said intermediate section of the core relative to the remainder of the core.

4. An absorbent article according to claim 3, wherein the intermediate section is movable in said direction toward the top sheet.

5. An absorbent article according to claim 3, wherein the intermediate section is movable from a position substantially on one side of the remainder of the absorbent core to a position substantially on the other side of the remainder of the absorbent core, so as to change the absorbent core from said first unconstrained form to said second unconstrained form.

6. An absorbent article according to claim 3, wherein the absorbent core includes a gap or unconnected portion through which the intermediate section may be passed from a position on one side of the absorbent core to a position on the other side, if necessary by elastically extending the top sheet and/or back sheet, and/or compressing the intermediate section and/or remainder of the absorbent core.

7. An absorbent article according to claim 6, wherein, when in said second form, a channel (7) is formed by a depression of said top sheet downwards towards the gap or disconnected portion (12) of the absorbent core (3).

8. An absorbent article according to claim 3, wherein the intermediate section has a dimension in the direction toward the top sheet which exceeds the dimension of the remainder of the absorbent core in the same direction.

9. An absorbent article according to claim 3, wherein a low-friction surface is provided on at least one of the intermediate section and the remainder of the absorbent core over at least part of a region where there is sliding touching movement therebetween.

10. An absorbent article according to claim 3 wherein the intermediate section includes resiliently compressible material.

11. An absorbent article according to claim 3 wherein a sheet of material is provided which passes over the side of the intermediate section proximate the top sheet and the side of the absorbent core proximate the back sheet and is attached such that it prevents the intermediate section from moving substantially in a lateral direction relative to said absorbent core when the intermediate section is positioned on the side of the absorbent core nearer the top sheet.

12. An absorbent article according to claim 1, wherein the material forming the intermediate section includes absorbent material, in particular superabsorbent material.

13. An absorbent article to claim 1, wherein the protrusion has a longitudinal dimension which is less than the longitudinal dimension of the core.

14. An absorbent article according to claim 1, in the form of a sanitary napkin.

15. The absorbent article according to claim 1, wherein said direction toward the top sheet is a vertical direction.

* * * * *